United States Patent [19]

Otten et al.

[11] Patent Number: 4,706,678
[45] Date of Patent: Nov. 17, 1987

[54] ELECTROCHEMICAL REFERENCE ELECTRODE

[75] Inventors: Josephus M. Otten, Miami, Fla.; Berend Boekema, Roden, Netherlands

[73] Assignee: Cordis Europa N.V., Roden, Netherlands

[21] Appl. No.: 21,546

[22] Filed: Mar. 2, 1987

Related U.S. Application Data

[63] Continuation of Ser. No. 704,612, Feb. 22, 1985, abandoned.

[30] Foreign Application Priority Data

Feb. 29, 1984 [NL] Netherlands .......................... 8400649

[51] Int. Cl.[4] ...................... G01N 27/36; A61B 5/00
[52] U.S. Cl. ...................................... 128/635; 204/435
[58] Field of Search ............... 128/635, 637, 642, 656, 128/620, 772; 204/421, 433, 435, 219, 1 T

[56] References Cited

U.S. PATENT DOCUMENTS

| | | | |
|---|---|---|---|
| 3,662,745 | 5/1972 | Cosentino | 128/635 |
| 3,676,319 | 7/1972 | Kirsten | 204/435 |
| 3,856,649 | 12/1974 | Genshaw et al. | 204/435 |
| 4,105,509 | 8/1978 | Jungck | 204/435 |
| 4,115,209 | 9/1978 | Freiser et al. | 204/1 T |
| 4,166,021 | 8/1979 | Ross, Jr. et al. | 204/1 T |
| 4,214,968 | 7/1980 | Battaglia et al. | 204/435 |
| 4,282,079 | 8/1981 | Chang et al. | 204/435 |
| 4,303,740 | 12/1981 | Petro et al. | 204/435 |
| 4,340,457 | 7/1982 | Kater | 128/635 |
| 4,432,366 | 2/1984 | Margules | 204/435 |
| 4,440,175 | 4/1984 | Wilkins | 128/635 |
| 4,552,625 | 11/1985 | Van Der Velden | 204/435 |

FOREIGN PATENT DOCUMENTS

2060896  5/1981  United Kingdom .

Primary Examiner—Edward M. Coven
Attorney, Agent, or Firm—Lockwood, Alex, Fitzgibbon & Cummings

[57] ABSTRACT

An electrochemical reference electrode having improved potential stability is provided, such reference electrode being suitable for use as a second-order or half-cell component within a system for measuring the ion concentration of body liquids. The reference electrode includes an electrode of the metal/metal cation type in association with an electrolyte that includes a soluble salt of the metal cation of the electrode, which soluble salt is present within the electrolyte in an amount sufficient to have metal cation present in the electrolyte at its saturation concentration.

6 Claims, 2 Drawing Figures

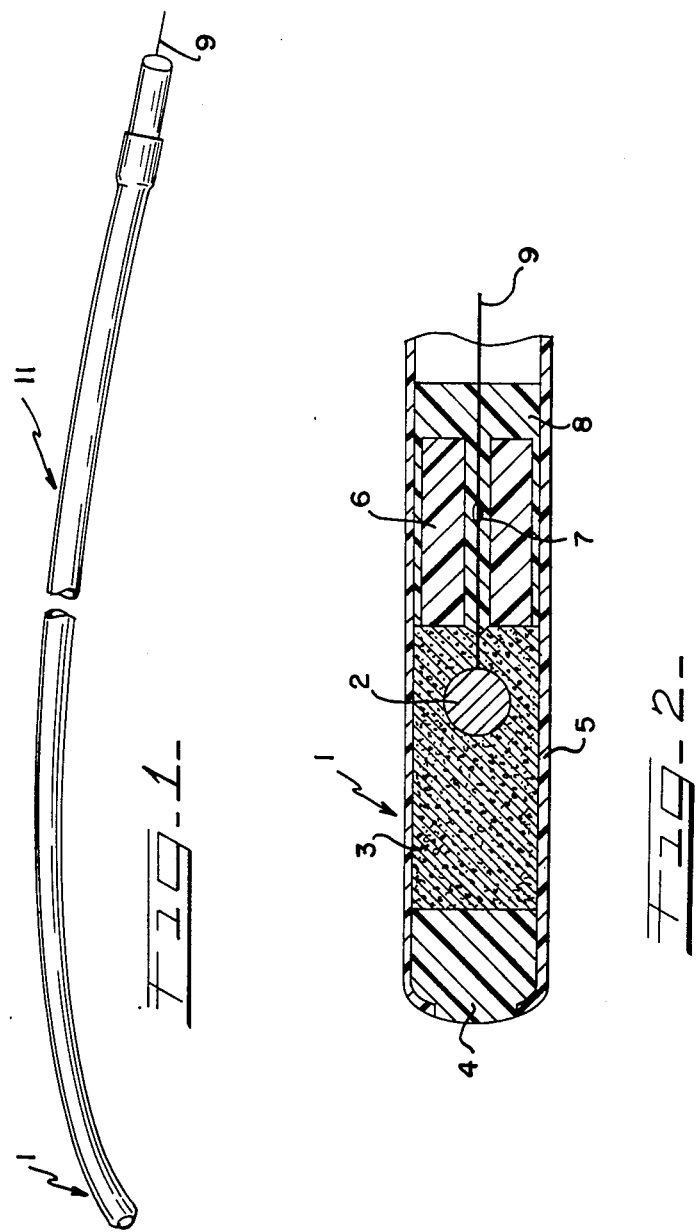

ELECTROCHEMICAL REFERENCE ELECTRODE

This application is a continuation, of application Ser. no. 704,612, filed Feb. 22, 1985, abandoned.

BACKGROUND AND DESCRIPTION OF THE INVENTION

The present invention generally relates to an electrochemical reference electrode, more particularly to an electrochemical, second-order reference electrode for a half cell that exhibits superior potential stability and that is of the type having a metal/metal salt electrode surrounded by and in contact with an electrolyte. The electrolyte includes a soluble salt of the electrode metal cation, such soluble salt being present within the electrolyte in an amount sufficient to have the metal cation present within the electrolyte at its saturation concentration. The soluble salt and the anion react within the electrolyte to form a substantially insoluble salt which is the metal salt of and which also deposits onto the electrode in order to maintain the equilibrium condition of the metal/metal salt electrode.

Various systems and electrodes have been devised and used in order to measure and monitor ion activity within liquids such as human blood. Such systems include half cells or second-oorder eleectrodes, these systems tyupically including a measuring electrode that is particularly sensitive to the ion to be measured, as well as a refereence electrode that is provided in order to establish a substantially accurate and constant comparative potential. Significant progress has been made in order to provide reference electrodes that exhibit substantial improvements in accuracy and constancy of the comparative potential that they provide. One approach in this regard is described in United Kingdom published patent application No. 2,060,896, which proposes improving the potential stability of a second-order reference electrode by including substantially specific amounts of free silver of the colloidal type within the electrolyte of this type of an electrode.

Often, reference electrodes of this type are used within systems for measuring and/or monitoring the hydrogen ion concentration, or pH, of a liquid such as blood. Known systems in this regard employ an ion-selective electrode, such as an Ag/AgCl electrode, as the reference electrode. Difficulties that are usually encountered in connection with using an ion-selective electrode as the reference electrode include the fact that they are susceptible to measuring errors, such as drift, and can have an undesirably short service life as the electrode gradually moves toward an advanced state of decay.

Ideally, a reference electrode should provide a steady reference potential, particularly when used for in vivo measurement and monitoring of physiologically important ion concentration parameters such as pH. Preferably, these types of devices are sized and structured so as to be capable of being placed in vivo within the bloodstream, typically by means of a catheter structure. These types of structures are superior to electrode systems by which a probe is adhered to the patient's skin, which systems can be inherently less accurate and also difficult to apply in connection with continuous blood analysis in extra-corporal blood circuits such as those utilized during hemodialysis and open-heart surgical procedures.

Typically, the measuring electrode in these types of systems will include a component that is selectively sensitive in an electrically reactive manner to the parameter being measured, such as blood pH. Exemplary components in this regard include a measuring electrode that incorporates an ion-sensitive field effect transistor (ISFET) transducer having an ion sensitivity to hydrogen ions to determine hydrogen ion concentration, or pH.

In connection with in vivo measurement of ion concentrations within body liquids, it is extremely critical that the reference electrode function to provide an accurately constant comparative potential. Inaccuracies can arise, together with consequent measuring errors, due to design and structural shortcomings, despite the thoroughly enhanced structural and design characteristics of present-day reference electrodes.

The present invention provides a reference electrode that is suitable for use within a system for in vivo ion concentration measurement and monitoring, such as that carried out within the bloodstream of a patient, which reference electrode does not experience substantial drift and which does provide an accurately constant comparative potential. The reference electrode includes an electrode component of the metal/metal salt type that is surrounded by and in contact with an electrolyte including the metal cation of the electrode, which electrolyte has added thereto a substantially soluble salt of the electrode metal cation, such being added in an amount sufficient to have the metal cation present in the electrolyte at a saturation concentration. These metal cations within the electrolyte react with anions within the electrolyte in order to form a substantially insoluble salt that is the salt of the electrode and which salt also deposits onto the electrode.

It is accordingly a general object of the present invention to provide an improved reference electrode which reduces the likelihood of having errors occur during ion concentration measurements, especially in vivo measurements of ion concentrations within body liquids.

Another object of the present invention is to provide an improved reference electrode as a second-order electrode of considerably enhanced operational characteristics, especially a substantial reduction in drift and a considerable prolongation of the service life of the reference electrode.

Another object of the present invention is to provide an improved reference electrode that can be useful in exhibiting recovery of electrodes that have progressed to the point at which they have entered an advanced state of decay.

Another object of the present invention is to provide a reference electrode that includes a silver/silver chloride electrode member within an electrolyte solution, which electrolyte solution enhances the rapid achievement of and the maintenance of the equilibrium of the silver chloride composition of the electrode member.

Another object of the present invention is to provide an improved catheter system that is suitable for in vivo measurement of body liquids, which catheter system includes a reference electrode that provides an especially accurate constant comparative potential.

These and other objects, features and advantages of this invention will be clearly understood through a consideration of the following detailed description.

BRIEF DESCRIPTION OF THE DRAWING

In the course of this description, reference will be made to the attached drawings, wherein:

FIG. 1 is an elevational view of a typical catheter structure suitable for incorporating an ion concentration measurement system that includes the reference electrode in accordance with this invention; and FIG. 2 is a longitudinal sectional view of the preferred reference electrode in accordance with this invention.

DESCRIPTION OF THE PARTICULAR EMBODIMENTS

FIG. 1 shows a catheter 11 of the type that is suitable for insertion into a human bloodstream and the like, which catheter 11 has a generally hollow top portion 1 within which the reference electrode according to this invention (FIG. 2) may be conveniently mounted. FIG. 1 illustrates just one of a variety of arrangements by which the reference electrode according to this invention may be mounted and positioned in connection with procedures used for measuring and monitoring ion concentrations within the bloodstream and the like by means of a system including this reference electrode which is in electrical communication with the remainder of the measuring or monitoring circuit or system by means of a conductive wire 9. Various arrangements are known in this regard and will be apparent to the skilled artisan. Although the invention is not limited to mounting of the reference electrode according to this invention within a catheter or within a catheter top as illustrated in FIG. 1, the results achieved by these embodiments are particularly relevant to and suitable for such embodiments.

With particular reference to FIG. 2, the reference electrode itself is mounted within the top 1 of the catheter 11, the reference electrode including a wall 5 within which is axially and substantially centrally mounted an electrode 2, which mounting is preferably facilitated by providing an axially centering plug 6. Electrode 2 is of a known type of metal/metal salt, typically a silver/silver chloride electrode. Electrode 2 is surrounded by and in contact with an electrolyte 3 having a suitable physical consistency, such as that of a gelled material. Electrolyte 3 is sealed at one end of the reference electrode structure by a plug 4 and at the other end by the axially centering plug 6 in association with a set-in-place seal 8, which may be made of an adhesive material such as an epoxy resin. Plug 4 is typically made of a material, such as polyhydroxyethyl methacrylate (pHEMA), that permits diffusion of ions therethrough and with respect to the bloodstream. The electrode 2 is electrically connected to the remainder of the measuring circuit (not shown) through the current conducting wire 9, typically in association with a soldering or welding joint 7.

Referring with more particularity to the electrolyte 3, such is of a substantially constant composition and contains an anion that reacts with a metal cation that is also within the electrolyte 3 in order to form a poorly soluble or substantially insoluble salt. A soluble salt of the metal cation is added to the electrolyte 3 in an amount sufficient to have the metal cation present in the electrolyte 3 at a saturated concentration. When the electrode member 2 is of the silver/silver chloride type, the anion present in the electrolyte 3 should be a chloride anion which reacts with silver cation present in the electrolyte in saturated concentration, while the soluble salt added to the electrolyte 3 would be a soluble silver salt such as silver nitrate, this soluble salt being provided in amount sufficient such that same contributes metal cations to the electrolyte 3 so that the metal cations, typically silver cations, are present at a saturation concentration. Also, chloride anions present within the electrolyte 3 preferably are present at a concentration that generally corresponds to that of blood, approximately 0.11 M per liter when the reference electrode is intended to be used within a system for in vivo ion concentration measurement and monitoring within the bloodstream of a patient.

In the preferred embodiment, wherein the electrode 2 is of the silver/silver chloride type and wherein the electrolyte 3 includes chloride ions and has silver nitrate added thereto, the following chemical reaction equations are relevant:

The solubility product of $AgCl=[Ag^+][Cl^-]$ is $1.8 \times 10^{-10}$ at 20°C.    (1)

$$AgCl \rightleftharpoons Ag^+ + Cl^- \quad (2)$$

$$Ag^{30} + e \rightleftharpoons Ag \quad (3)$$

$$AgNO_3 + Cl^- \rightleftharpoons AgCl \downarrow + NO_3^- \quad (4)$$

$$2Ag + O_2 \rightleftharpoons 2AgO \quad (5)$$

By adding silver nitrate in the form of a diluted solution having a concentration of, for example about $10^{-6}$ M, excess silver will precipitate or deposit in accordance with equation (4) so that a saturated silver cation solution containing the thus-formed silver chloride is provided. Experiments have shown that, in such an electrolyte 3, the chemical equilibrium condition illustrated by reaction equation (2) is established very rapidly. Consequently, drift occurring as a result of the equilibrium condition being established is significantly reduced. Moreover, the risk of a slow but continuous decay of the silver/silver chloride electrode which would be cuased by diffusion of silver cations through the plug 4 and into the bloodstream or the like is reduced inasmuch as the supplementation of the silver cation does not originate from the silver chloride deposited on the electrode itself, but the silver cation instead originates from the silver chloride present in the electrolyte 3. As a result, the service life of the reference electrode is prolonged considerably.

Another difficulty of interest capable of being avoided according to the reference electrode of this invention is that efficient and long-lasting operation of a silver/silver chloride electrode may additionally be caused by the occurence of leakage currents flowing between the ISFET and the reference electrode, which leakage currents can occur for example when using an ISFET measuring electrode within the measuring circuit. Furthermore, leakage may occur in the form of electrolyte migration through the seal 8 and to the soldering or welding joint 7, as a result of which a galvanic cell is formed between this soldering or welding joint 7 and the silver chloride of the reference electrode.

Either or both of these disadvantages will result in having the silver chloride reduced to thereby form silver metal generally in accordance with reaction equation (3), which silver mixes with the layer of silver chloride already present. The silver metal converts partially back into silver chloride in the course of time due to reaction equation (3), followed by reaction equation (2), so forming in said course of time a thin film of silver chloride onto the silver metal. When, in accordance with the present invention, a saturated silver cation solution is provided by the addition of silver nitrate, this formation of the silver chloride onto the silver has been found to occur substantially instantaneously. Consequently, there is substantially no experience of voltage variations that can be caused by the presence of a mixture of silver and silver chloride and the appurtenant mixing potential thereof being different from the potential of pure AgCl.

An additional advantage of the important aspect of the present invention wherein silver cations are added to the electrolyte by means of a soluble salt thereof is that the electrode potential becomes less dependent upon the partial oxygen pressure. By virtue of reaction equation (5) hereinabove, the electrode potential of pure silver is a function of the partial oxygen pressure; accordingly, a mixture of silver and silver chloride is likewise a function of this partial oxygen pressure.

It will be understood that the embodiments of the present invention which have been described are merely illustrative of a few of the applications of the principles of the present invention. Numerous modifications may be made by those skilled in the art without departing from the true spirit and scope of the invention.

We claim:

1. An electrochemical reference electrode having improved potential stability, comprising:
   an enclosure;
   an electrode member mounted within the enclosure, said electrode member being made of a metal and a salt of said metal in substantial equilibrium with each other, the cation of said metal being capable of participating in a reversible chemical reaction;
   an electrolyte that is in contact with said electrode member, said electrolyte being an equilibrium maintaining component that is a liquid solution of a substantially constant composition and containing an anion which forms a substantially insoluble compound with said metal cation of the electrode member, said anion being the anion of said metal salt of the electrode member, said electrolyte having added thereto a soluble salt of said metal cation, which soluble salt is present within the electrolyte at a concentration that is sufficient to have said metal cation present within the electrolyte at its saturation concentration to thereby rapidly form said substantially insoluble compound in order to maintain same at it saturation concentration within the electrolyte and deposit same onto said electrode member in order to substantially maintain said equilibrium between said metal and said metal salt of the electrode; and
   means for electrically connecting the electrode member to a system for measuring the ion concentration of a liquid.

2. The electrochemical reference electrode according to claim 1, wherein said electrode member is of the silver/silver chloride type, said anion that forms a substantially insoluble compound with the metal cation is a chloride anion, and wherein the soluble salt of the metal cation that is added to the electrolyte is silver nitrate.

3. The electrochemical reference electrode according to claim 1, wherein the electrolyte anion that forms the substantially insoluble compound with the metal cation of the electrode member is the chloride anion, and wherein said chloride anion is present within the electrolyte at a concentration that substantially corresponds to the concentration of chloride anions within blood.

4. A catheter for effecting in vivo measurement of ion concentrations within body liquids, which catheter includes an electrochemical reference electrode, comprising:
   an enclosure;
   an electrode member mounted within the enclosure, said electrode member being made of a metal and a salt of said metal in substantial equilibrium with each other, the cation of said metal being capable of participating in a reversible chemical reaction;
   an electrolyte that is in contact with said electrode member, said electrolyte being an equilibrium maintaining component that is a liquid solution of a substantially constant composition and containing an anion which forms a substantially insoluble compound with said metal cation of the electrode member, said anion being the anion of said metal salt of the electrode member, said electrolyte having added thereto a soluble salt of said metal cation, which soluble salt is present within the electrolyte at a concentration that is sufficient to have said metal cation present within the electrolyte at its saturation concentration to thereby readily form said substantially insoluble compound and in order to maintain same at its saturation concentration within the electrolyte and deposite same onto said electrode member in order to substantially maintain said equilibrium between said metal and said metal salt of the electrode; and
   means for electrically connecting the electrode member to a system for measuring the ion concentration of a liquid.

5. The catheter according to claim 4, wherein said electrode member is of the silver/silver chloride type, said anion that forms a substantially insoluble compound with the metal cation is a chloride anion, and wherein the soluble salt of the metal cation that is added to the electrolyte is silver nitrate.

6. The catheter according to claim 4, wherein the electrolyte anion that forms the substantially insoluble compound with the metal cation of the electrode member is the chloride anion, and wherein said chloride anion is present within the electrolyte at a concentration that substantially corresponds to the concentration of chloride anions within blood.

* * * * *

UNITED STATES PATENT AND TRADEMARK OFFICE
CERTIFICATE OF CORRECTION

PATENT NO. : 4,706,678

DATED : Nov. 17, 1987

INVENTOR(S) : Otten et al.

It is certified that error appears in the above-identified patent and that said Letters Patent is hereby corrected as shown below:

Col. 4, line 22, "$Ag^{30}$" should read --$Ag^+$--.

Signed and Sealed this

Thirteenth Day of December, 1988

Attest:

DONALD J. QUIGG

*Attesting Officer*  *Commissioner of Patents and Trademarks*